United States Patent
Zhang et al.

(10) Patent No.: US 9,863,031 B2
(45) Date of Patent: Jan. 9, 2018

(54) METHOD FOR PREPARING A COATING OF THE SURFACE OF MEDICAL DEVICES MADE OF NICKEL-TITANIUM ALLOY

(75) Inventors: DeYuan Zhang, Shenzhen (CN); YueHui Xie, Shenzhen (CN)

(73) Assignee: Lifetech Scientific (Shenzhen) Co., Ltd. (CN)

( * ) Notice: Subject to any disclaimer, the term of this patent is extended or adjusted under 35 U.S.C. 154(b) by 2724 days.

(21) Appl. No.: 12/312,769

(22) PCT Filed: Nov. 27, 2006

(86) PCT No.: PCT/CN2006/003171
§ 371 (c)(1),
(2), (4) Date: Nov. 15, 2010

(87) PCT Pub. No.: WO2008/064517
PCT Pub. Date: Jun. 5, 2008

(65) Prior Publication Data
US 2012/0094143 A1    Apr. 19, 2012

(51) Int. Cl.
| | | |
|---|---|---|
| C23C 14/00 | (2006.01) |
| C23C 14/32 | (2006.01) |
| C23C 14/02 | (2006.01) |
| A61L 27/06 | (2006.01) |
| A61L 27/30 | (2006.01) |
| C23C 14/06 | (2006.01) |
| A61L 31/08 | (2006.01) |

(52) U.S. Cl.
CPC ............ *C23C 14/024* (2013.01); *A61L 27/06* (2013.01); *A61L 27/306* (2013.01); *A61L 31/082* (2013.01); *A61L 2300/608* (2013.01); *A61L 2400/16* (2013.01); *C23C 14/0641* (2013.01); *Y10T 428/12493* (2015.01)

(58) Field of Classification Search
CPC . C23C 14/024; C23C 14/0641; A61L 31/082; A61L 2300/608
See application file for complete search history.

(56) References Cited

U.S. PATENT DOCUMENTS

2002/0102400 A1* 8/2002 Gorokhovsky ....... C23C 14/022
428/336

OTHER PUBLICATIONS

D Starosvetsky, I Gotman, Corrosion behavior of titanium nitride coated Ni—Ti shape memory surgical alloy, Biomaterials, vol. 22, Issue 13, Jul. 2001, pp. 1853-1859, ISSN 0142-9612.*

* cited by examiner

Primary Examiner — Ibrahime A Abraham
(74) Attorney, Agent, or Firm — Raymond Sun

(57) ABSTRACT

Provided is a method for plating a biocompatible coating with nano structure on the surface of a nickel-titanium shape memory alloy, particularly a method suitable for plating a coating on the surface of medical devices made of nickel-titanium alloy. The method includes the following steps: heat treating, surface pretreating, ion sputter cleaning, depositing a pseudodiffusion layer, plating a sub-layer film, plating a pure TiN layer, and so on. The coating has the following advantages: 1) it could deform in response to the deformation of substrate without delaminating and cracking; 2) it has less resistance to the deformation of substrate; 3) it has less penetrable holes so as to reduce the dissolution of nickel into bio-body through these holes; 4) the coating has better biocompatibility compared to the substrate material.

9 Claims, No Drawings

METHOD FOR PREPARING A COATING OF THE SURFACE OF MEDICAL DEVICES MADE OF NICKEL-TITANIUM ALLOY

TECHNICAL FIELD

The present invention pertains to a method for forming a biocompatible nano-structure coating on the surface of a nickel-titanium shape memory alloy. The present invention is particularly suitable as a method for plating a coating on the surface of medical devices made of nickel-titanium alloy.

BACKGROUND TECHNOLOGY

Conventional shape memory alloy technology and heat treatment technology as well as the shape memory effect of materials were reported by F. Johnson in 1920. The shape memory effect of nickel-titanium alloy was reported by W. J. Buehler et al. (US Naval Ordnance Laboratory) in 1963. In 1966, J. A. Zijderveld was the first to use phase transformation theory to explain the shape memory effect. The shape memory effect can cause a material to switch between two shapes through temperature variation or provide a material with super-elasticity (elasticity that is much greater than that of a conventional material of the same type) through phase transformation. A generic nickel-titanium shape memory alloy is a binary alloy composed of nickel and titanium in equal atomic ratios. It is possible to adjust the characteristic phase transformation temperature and properties by appropriately adjusting the Ni—Ti ratio. In some cases, other elements, such as copper or niobium, replace part of the titanium to change its properties or phase transformation temperature.

In order to produce the shape memory effect, it is necessary to rigorously heat-treat the nickel-titanium alloy. Usually, a shape is first produced through a high-temperature heat treatment (hot rolling, hot forging, or hot extraction), followed by cold deformation to the required shaped. Then, said shape is fixed, and the temperature is kept in the range of 420-550° C. for a certain period of time. In this case, the part can switch between the aforementioned two shapes.

In 1991, Parodi and colleagues used a nickel-titanium alloy to treat abdominal aortic aneurysms. In 1993, Cragg and Dake used a Dacron-coated nickel-titanium alloy as the material for stents. Some of these designs exploit the shape memory effect, while others exploit super-elasticity.

It is well known that nickel is highly toxic to biological organisms. Although nickel-titanium alloy is not as toxic as nickel, research has shown that in many cases, nickel-titanium is harmful to the human body. Its long-term effects are still being studied. Titanium, on the other hand, is a metal that exhibits very good biocompatibility. Therefore, great efforts have been made to cover surfaces with titanium or titanium compounds and other materials that exhibit good biocompatibility. The methods that have been used include the following: 1) metal or metal ceramic is formed on a surface, for example, TiN is formed in a nitrogen-containing atmosphere or medium at high temperature or TiN is formed on the surface by the injection of nitrogen ions; 2) a polymeric material, such as Teflon, is coated on the surface; 3) an inorganic compound, for example, hydroxyapatite is sprayed on the surface. The surface treatment of shape memory alloys has the following difficulties:

a) temperature control: processing should not destroy the crystal structure of the material; otherwise, the shape memory effect or super-elasticity will be reduced or disappear;

b) toughness of the surface coating: since a shape memory alloy will undergo shape transformation during use, the surface coating must be able to deform with the deformation of the nickel-titanium alloy;

c) good adhesion: the surface coating must deform in response to the deformation of the nickel-titanium alloy without delaminating;

d) low transformation resistance: the surface coating should not hinder the shape transformation of the nickel-titanium;

e) low porosity: only a compact film can effectively improve corrosion resistance and biocompatibility and reduce or prevent elution of the nickel into the biological organism.

The objective of the present invention is to provide a method for coating TiN on the surface of medical devices made of nickel-titanium alloy. The obtained coating is compact, has high adhesion, and can deform with the deformation of the nickel-titanium alloy a finite number of times without cracking or delaminating. Its resistance to deformation of nickel-titanium is within an acceptable range. The treatment process does not adversely affect the shape memory effect or super-elasticity of the nickel-titanium alloy.

CONTENT OF THE INVENTION

The objective of the present invention is realized through the following technical scheme. The method for coating the surface of medical devices made of a nickel-titanium alloy disclosed in the present invention comprises the following steps:

(1) heat treatment: the medical device on which the coating is to be applied is heat-treated.

(2) surface pretreatment: the surface is cleaned of oxides and other contaminants;

(3) ion sputter-cleaning: the pretreated medical device is placed in a vacuum chamber; argon gas is supplied to the chamber and a negative bias voltage is applied; glow discharge plasma is used to perform ion sputter-cleaning of its surface;

(4) deposition of pseudo-diffusion layer: after ion sputter-cleaning, one or more cold cathode vacuum arc ion sources equipped with a filtering device are turned on;

(5) plating of sub-layer film: after the pseudo-diffusion layer is formed, pure titanium and titanium-titanium nitride are alternately plated;

(6) selection of number of repetition times: it is possible to repeat step (5) multiple times depending on the product size and the deformation conditions;

(7) plating of pure titanium nitride layer: one or more ion sources are turned on to plate a pure titanium nitride layer with a thickness in the range of 200-400 nm; after the desired thickness is reached, the ion sources are turned off and the supply of gas and the application of the bias voltage are stopped.

During ion sputter-cleaning in step (3) of the present invention, the pretreated medical device is placed in a vacuum chamber, 2-4 Pa of argon gas is supplied to the chamber, and a negative bias voltage of 500-1600 V is applied.

In step (4) of the present invention, the partial pressure of the argon gas is adjusted to $10^{-1}$-$10^{-3}$ Pa, the bias voltage is adjusted between −400 and −600 V, and the current is controlled in the range of 40-100 A to deposit the pseudo-diffusion layer. The time is determined based on the production technology and is usually in the range of 20-120 s.

The thickness is controlled to 100-200 nm. For small and intricate devices, the time should be short, the arc current low, and the deposition divided into several cycles. After the deposition has been completed, the ion sources are turned off and remain off for 20 s or longer.

In step (5) of the present invention, pure titanium and titanium nitride are alternately plated. That is, the pressure of the argon gas is adjusted to $1-5\times10^{-1}$ Pa and the bias voltage is adjusted to 400-600 V. One or more ion sources are turned on and the arc current is controlled in the range of 40-100 A to carry out etching. The bias voltage is quickly reduced to 50-200 V after 10-40 s to plate the pure titanium layer. When the thickness reaches 40-100 nm, the ion sources are turned off, nitrogen gas is supplied at a flow rate of 10-40 SCCM and the ion sources are turned on again to plate the titanium and titanium nitride mixture layer. The thickness is controlled in the range of 40-100 nm. Once the desired thickness is reached, the ion sources are turned off and remain off for 20-120 s; the next sub-layer is then plated. Said step (5) can be repeated 1-20 times depending on the technical requirements. If the product is large, the deformation is low, and a small number of penetrable holes is required, the upper limit of the number of repetition times should be selected. If the coating is required to have low resistance to deformation and the product is to undergo significant deformation, the lower limit of the number of repetition times should be selected.

In the aforementioned nano-structured coating formation process, after the required number of repetition times in steps (5), (6) has been completed, the flow rate of the argon gas is reduced to 20 SCCM. The flow rate of the argon gas is adjusted so that the vacuum level in the furnace is $2-20*10^{-1}$ Pa. The bias voltage is adjusted between $-100$ and $-300$ V. One or more ion sources are turned on to plate the pure titanium nitride layer. Said coating is a nano-structured Ti—N—O coating. Said nano-structured coating is composed of sub-layers with a thickness in the range of 40-100 nm. Each said sub-layer has a different composition: the lowermost layer is a pure titanium layer, and the pseudo-diffusion layer is formed by the nickel-titanium alloy; the intermediate layer alternates between a pure titanium layer and the layer formed by the mixture of titanium and titanium nitride; the upper layer is a pure titanium nitride layer, which can also be titanium oxide or a mixture of titanium oxide and titanium nitride. The processing parameters for forming said nano-structured coating are highly dependent upon the specific surface area of the nickel-titanium product. For a rod-shaped or thread-shaped product with low specific surface area, the upper limit of the pressure, the lower limit of the absolute value of the bias voltage, and the lower limit of the thickness are selected.

Compared with the conventional technology, the present invention has the following advantages: 1) the coating can deform in response to the deformation of the substrate without cracking or delaminating; 2) the coating has less resistance to deformation of the substrate; 3) it has fewer penetrable holes so that elution of nickel into biological organism through said holes can be reduced; 4) the coating exhibits better biocompatibility than the substrate material.

SPECIFIC APPLICATION EXAMPLE

1) Equipment Type and Technical Requirements

The technology used by the present invention is filtered cold cathode vacuum arc ion plating. That is, under high vacuum conditions, a filtered cold cathode vacuum arc is used to evaporate and ionize titanium. Then, under the effect of an applied bias voltage, the titanium moves toward the surface of the nickel-titanium alloy medical device. The titanium reacts with nitrogen gas to form a TiN layer on the surface. The equipment must include the following:

a) Vacuum system: Vacuum level better than $6\times10^{-3}$ Pa;

b) A workstation that can rotate to ensure uniformity of the surface coating;

c) Bias voltage power supply: 1000 V;

d) Cold cathode vacuum arc ion source with filter and power supply system: the ion source is equipped with a water-cooling apparatus and a magnetic field for arc control;

e) Gas supply system: at least two gas supply pipes are used to supply nitrogen gas and argon gas; each gas supply pipe is equipped with a gas source, depressurized gas, an electromagnetic valve, a mass flowmeter, and a controller.

The advantage of this technology is its high ionization rate. It is very easy to adjust the ion state by adjusting the bias voltage and the vacuum level so that it can be used for sputter etching, heating, and film deposition plating. The formed film layer has a compact, controllable structure, and exhibits good adhesion, but the disadvantage of this technology is the high thermal effect of the ions. When the ions strike the product surface, energy is transferred as heat to the product, which raises its temperature. Specifically, the temperature of a product with a large specific surface area may rise to a very high level in a very long [sic; short] time. Generally speaking, in the case of ion plating, the temperature of the product cannot be accurately measured. The temperature rise of the product can only be controlled by controlling the process parameters.

All of the aforementioned technical requirements cannot be fulfilled by a single uniform TiN layer; therefore the present invention uses a gradient coating with different constituent layers. The sub-layer that is immediately adjacent to the nickel-titanium alloy substrate is a transition layer. The composition changes from nickel-titanium alloy to pure titanium, which is used to improve adhesion of the film layer. It is usually composed of alternating layers of pure titanium and a mixture of Ti+TiN. The pure titanium layers exhibit good compactness and toughness and have a low modulus of elasticity. The small amount of TiN creates a transition from pure titanium to pure TiN on the surface in order to facilitate cooling after plating and ion etching. It can block the crystal particles in the adjacent titanium layer, specifically, block and etch the crystal particles with growth advantage. The uppermost surface is a pure TiN layer, which can improve the chemical stability and biocompatibility of the product.

In the transition layer between the pure titanium layer and pure titanium nitride layer, the thickness of the alternating sub-layer is in the range of 40-100 nm. The total thickness is in the range of 0.5-2 μm. The thickness of the sub-layer and the total thickness vary depending on product size (such as thread or rod diameter) and the required deformation degree. For a product of relatively large thickness or size, or a small deformation degree, the sub-layer can be relatively thick. The reason for this is that because the product is large and thick, first, the temperature rises slowly during film plating so that the film plating time can be extended continuously, and second, a large deformation driving force is used, which can drive the relatively thick film layer to deform coincidentally. Of course, as the total thickness increases, the number of penetrable holes is reduced, but the deformation resistance is increased so that the possibility of cracking or delaminating also increases.

2) Process and Technical Parameters a) Pre-treatment: the oxide and contaminants are removed from the surface.

b) The clean nickel-titanium alloy product is placed on a workstation that can revolve and rotate in the vacuum chamber.

c) The vacuum chamber is closed and evacuated to $6.6 \times 10^{-3}$ Pa.

d) Argon gas is introduced until the vacuum level goes to 2-4 Pa. The bias voltage power supply is turned on to slowly raise the voltage to 900 V. The nickel-titanium product is then in a glow discharge plasma and is cleaned by ions. If there are frequent sparks, the raising of the bias voltage is temporarily suspended. The voltage is raised after the discharge stabilizes.

e) After the voltage is raised to 900 V, that state is maintained for 10 min. The argon gas is reduced to keep the vacuum level to $1-5 \times 10^{-2}$ Pa. The bias voltage is adjusted to 400-600 V. One or more ion sources are turned on and the arc current is maintained at 60 A to plate a titanium mixture layer with a thickness in the range of 100-200 nm.

f) After the required thickness is reached, the ion sources are turned off for 40 s.

g) The argon gas is adjusted so that the vacuum level becomes Pa [sic]. The bias voltage is adjusted to 400 V and the ion source is turned on to perform etching. This state is maintained for 10-40 s.

h) The bias voltage is quickly lowered to 50-200 V to plate the pure titanium layer with a thickness in the range of 40-100 μm.

i) The ion source is turned off for 20-100 s.

j) Argon gas is supplied at a flow rate of 20-40 SCCM. The ion source is turned on to plate the Ti+TiN mixed layer with a thickness in the range of 40-100 μm.

k) The ion source is turned off for 20-100 s.

l) Steps g)-k) are repeated as required.

m) The flow rate of the argon gas is adjusted to 20 SCCM. The argon gas is adjusted so that the vacuum level goes to 0.5-2 Pa. The bias voltage is adjusted to 100-250 V. The ion source is turned on to plate a TiN layer to 100-400 μm.

n) The device is cooled and removed from the furnace, and the quality of the coating layer is inspected.

3) Coating Layer Defects and Countermeasures Thereto a) Deterioration of deformability: One possibility is that the temperature was too high during the film plating process, which led to a change in the crystal structure of the nickel-titanium alloy. As a result, the shape memory or super-elasticity effect deteriorates. Another possibility is that the coating layer exhibits excessive deformation resistance. In the first case, the ion source current and bias voltage should be reduced during the etching and film plating processes to reduce the input energy or the film plating time. In the second case, the number of times that the intermediate transition layer is formed is reduced to reduce the overall thickness.

b) The coating layer delaminates or cracks during deformation process

The coating layer is too thick or adhesion is insufficient. In the first case, the number of times that the intermediate transition layer is formed is reduced to reduce the overall thickness. In the second case, the time for forming the mixed layer or the intermediate etching time is extended.

Application Example 1

The process of plating coating layer on the surface of an occluder (diameter is smaller than 1 mm):

| Step | Pressure PA | Ar flow rate SCCM | N flow rate SCCM | Negative bias voltage -V | Current of the ion source A | Duration time S | Note |
|---|---|---|---|---|---|---|---|
| 1. Evacuation | $6 \cdot 10^{-3}$ | 0 | 0 | 0 | 0 | — | |
| 2. Glow discharge cleaning | 1.6 | — | 0 | 900 | 0 | 600 | |
| 3. Evacuation | $6 \cdot 10^{-3}$ | 0 | 0 | 0 | 0 | — | |
| 4. Pseudo-diffusion layer | — | 20 | 0 | 450 | 50 | 20 | |
| 5. Stop | — | 20 | 0 | 450 | 0 | 20 | |
| 6. Etching | — | 20 | 0 | 400 | 60 | 10 | 12. These steps are repeated 10 times |
| 7. Pure titanium layer | 0.4 | — | 0 | 100 | 60 | 40 | |
| 8. Stop | 0.4 | — | 0 | 100 | 0 | 40 | |
| 9. Mixed layer | 0.5 | 20 | — | 100 | 60 | 40 | |
| [1]0. Stop | 0.5 | 20 | — | 100 | 0 | 40 | |
| 11. Titanium nitride layer | 0.6 | 20 | — | 200 | 60 | 240 | |

In this table, — means that the parameter concerned is controlled by other parameters or controls other processing parameters Application Example 1 [Sic]

The process of plating coating layer on the surface of vena cava filter (diameter is 2-5 mm)

| Step | Pressure PA | Ar flow rate SCCM | N flow rate SCCM | Negative bias voltage -V | Current of the ion source A | Duration time S | Note |
|---|---|---|---|---|---|---|---|
| 1. Evacuation | $6 \cdot 10^{-3}$ | 0 | 0 | 0 | 0 | — | |
| 2. Glow discharge cleaning | 1.6 | — | 0 | 900 | 0 | 600 | |
| 3. Evacuation | $6 \cdot 10^{-3}$ | 0 | 0 | 0 | 0 | — | |
| 4. Pseudo-diffusion layer | — | 20 | 0 | 450 | 60 | 40 | |
| 5. Stop | — | 20 | 0 | 450 | 0 | 40 | |
| 6. Etching | — | 20 | 0 | 400 | 60 | 40 | 12. These steps are repeated 15 times |
| 7. Pure titanium layer | 0.3 | — | 0 | 100 | 60 | 60 | |
| 8. Stop | 0.3 | — | 0 | 100 | 0 | 60 | |
| 9. Mixed layer | 0.4 | 20 | — | 100 | 60 | 60 | |
| [1]0. Stop | 0.4 | 20 | — | 100 | 0 | 60 | |
| 11. Titanium nitride layer | 0.6 | 20 | — | 200 | 60 | 240 | |

In this table, — means that the parameter concerned is controlled by other parameters or controls other processing parameters The method adopted by the present invention is filtered cold cathode vacuum arc vapor phase deposition technology. That is, a cold cathode vacuum arc is used to evaporate and ionize titanium metal. The titanium liquid droplets are filtered by a filtering apparatus, while the titanium ions are extracted and allowed to react with the supplied $N_2$, $O_2$ to form a coating on the nickel-titanium alloy. In order to reduce the number of penetrable holes, improve the toughness of the coating, lower the resistance of the coating to substrate deformation, and also to ensure that no new phase deposition occurs in the substrate material during the deposition process of the coating so that the shape memory effect will not be adversely affected, the coating is designed as a nano-structure: the inner layer is a mixture of pure titanium and the substrate component in order to reduce the surface stress and improve the adhesion of the coating; the intermediate layer is composed of plural layers of pure titanium layer+mixture layer of titanium and titanium nitride (or titanium oxide); the multi-layer structure design can reduce the number of penetrable holes and improve the coincidental deformability of the coating layer with the substrate; the outer layer is pure titanium nitride (or titanium oxide), which is used to improve biocompatibility. The thickness of each layer is in the range of 40-100 nm. The number of intermediate layers is selected in the range of 1-20 depending on the detailed requirement. As the number of the intermediate layers is increased, the number of penetrable holes is reduced, but the resistance to substrate deformation increases, the coincidental deformability deteriorates, and the possibility of cracking or delaminating occurring during deformation increases. In order to prevent the outer layer from growing beyond the inner layer, to reduce the surface roughness of the coating, and to reduce the number of penetrable holes, before a new layer is begun to be plated, the temperature of the substrate is always lowered to room temperature, and a high bias voltage is applied to perform etching. Then, after the temperature is raised, the film is plated. During film plating, before the temperature of the substrate rises to the aging temperature of the substrate, film plating is stopped.

The invention claimed is:

1. A method for preparing a coating on the surface of medical devices made of nickel-titanium alloy, characterized by the following steps:
   (1) heat-treating the medical device on which a film will be plated;
   (2) removing surface oxides and other contaminants from the surface of the medical device;
   (3) placing the pretreated medical device in a vacuum chamber, introducing argon gas into the chamber and applying a negative bias voltage, then using a glow discharge plasma to perform ion sputter-cleaning of the surface;
   (4) after ion sputter-cleaning, turning on one or more cold cathode vacuum arc ion sources that are equipped with a filtering apparatus to form a pseudo-diffusion layer that is formed by a mixture of pure titanium and the nickel-titanium alloy;
   (5) after the pseudo-diffusion layer is formed, alternately plating pure titanium and a mixture of titanium and titanium nitride;
   (6) repeating step (5);
   (7) turning on one or more ion sources to plate a pure titanium nitride layer with a thickness in the range of 200-400 nm, and then the ion sources are turned off and the supply of gas and the application of bias voltage are stopped.

2. The method for preparing a coating on the surface of medical devices made of nickel-titanium alloy described in claim 1 wherein during ion sputter-cleaning performed in step (3), the pretreated medical device is placed into a vacuum chamber, 2-4 Pa of argon gas is supplied to the chamber, and a negative bias voltage of 500-1600 V is applied.

3. The method for preparing coating on the surface of medical devices made of nickel-titanium alloy described in claim 1 wherein in step (4), the partial pressure of the argon gas is adjusted to between $10^{-1}$ and $10^{-3}$ Pa, the bias voltage is adjusted between −400 and −600 V, and the current is controlled in the range of 40-100 A to deposit the pseudo-diffusion layer; the time is in the range of 20-120 s; the thickness is controlled in the range of 100-200 nm; after completing the deposition, the ion sources are turned off for 20 s or longer.

4. The method for preparing a coating on the surface of medical devices made of nickel-titanium alloy described in claim 1 wherein in step (5), pure titanium and titanium nitride are plated alternately with the pressure of the argon gas is adjusted to $1-5\times10^{-1}$ Pa and the bias voltage adjusted to 400-600 V; one or more ion sources are turned on and the arc current is controlled in the range of 40-100 A to carry out etching; the bias voltage is reduced to 50-200 V after 10-40 s to plate the pure titanium layer; when the thickness reaches 40-100 nm, the ion sources are turned off, nitrogen gas is supplied at a flow rate of 10-40 SCCM and the ion sources are again turned on to plate the titanium and titanium nitride mixture layer; the thickness is controlled in the range of 40-100 nm.

5. The method for preparing a coating on the surface of medical devices made of nickel-titanium alloy described in claim 1 wherein step (5) is repeated 1-20 times.

6. The method for preparing a coating on the surface of medical devices made of nickel-titanium alloy described in claim 1 wherein after the repetition times in steps (5), (6), have been completed, the flow rate of the argon gas is reduced to 20 SCCM; the flow rate of a nitrogen gas is adjusted so that the vacuum level in the chamber becomes $2-20*10^{-1}$ Pa; the bias voltage is adjusted between −100 and −300 V; and one or more ion sources is turned on to plate the pure titanium nitride layer.

7. The method for preparing a coating on the surface of medical devices made of nickel-titanium alloy described in claim 6 wherein said coating is a nano-structured Ti—N—O coating.

8. The method for preparing a coating on the surface of medical devices made of nickel-titanium alloy described in claim 7 wherein said nano-structured coating is composed of sub-layers with a thickness in the range of 40-100 nm.

9. The method for preparing a coating on the surface of medical devices made of nickel-titanium alloy described in claim 8 wherein each said sub-layer has a varying composition: the lowermost layer is the pseudo-diffusion layer; the intermediate layer is alternately a pure titanium layer and a layer formed by a mixture of titanium and titanium nitride; the uppermost layer is a pure titanium nitride layer; said titanium nitride can also be titanium oxide or a mixture of titanium oxide and titanium nitride.

* * * * *